US012599626B2

(12) United States Patent　　　　(10) Patent No.: US 12,599,626 B2
Shiyan et al.　　　　　　　　　　　(45) Date of Patent:　Apr. 14, 2026

(54) METHOD OF OBTAINING A PHARMACEUTICAL AGENT USED FOR INHIBITING THE PROLIFERATION OF TUMOR CELLS

(71) Applicant: Fedor Zotov, Granada Hills, CA (US)

(72) Inventors: Lyudmila Nikolaevna Shiyan, Tomsk (RU); Galina Leonidovna Lobanova, Tomsk (RU); Alexey Vitalievich Pustovalov, Tomsk (RU); Mikhail Alexandrovich Buldakov, Tomsk (RU); Tatiana Alexandrovna Yurmazova, Tomsk (RU); Fedor Zotov, Granada Hills, CA (US); Dmitry Igorevich Shvartsman, Tomsk (RU); Anastasia Alekseevna Evtina, Tomsk (RU)

(73) Assignee: LIMITED LIABILITY COMPANY "LABORATORY OF INNOVATIVE TECHNOLOGIES", Moscow (RU)

( * ) Notice: Subject to any disclaimer, the term of this patent is extended or adjusted under 35 U.S.C. 154(b) by 325 days.

(21) Appl. No.: 18/259,175

(22) PCT Filed: Jan. 10, 2022

(86) PCT No.: PCT/RU2022/050003
§ 371 (c)(1),
(2) Date: Jun. 23, 2023

(87) PCT Pub. No.: WO2022/149998
PCT Pub. Date: Jul. 14, 2022

(65) Prior Publication Data
US 2024/0066058 A1　　Feb. 29, 2024

(30) Foreign Application Priority Data

Jan. 11, 2021　(RU) ........................... RU2021100394

(51) Int. Cl.
*A61K 33/26*　　(2006.01)
*A61P 35/00*　　(2006.01)
*B22F 1/052*　　(2022.01)
*B22F 1/054*　　(2022.01)
*B22F 1/145*　　(2022.01)
*B22F 9/14*　　(2006.01)

(52) U.S. Cl.
CPC .............. *A61K 33/26* (2013.01); *A61P 35/00* (2018.01); *B22F 1/052* (2022.01); *B22F 1/056* (2022.01); *B22F 1/147* (2022.01); *B22F 9/14* (2013.01); *B22F 2301/35* (2013.01); *B22F 2304/054* (2013.01); *B22F 2304/10* (2013.01); *B22F 2998/10* (2013.01)

(58) Field of Classification Search
CPC ......... A61K 33/26; A61P 35/00; B22F 1/052; B22F 1/056; B22F 1/147; B22F 9/14;
B22F 2301/35; B22F 2304/054; B22F 2304/10; B22F 2998/10; B22F 1/054; B22F 2999/00; B82B 3/00
See application file for complete search history.

(56) References Cited

U.S. PATENT DOCUMENTS

| | | | |
|---|---|---|---|
| 6,398,125 | B1 | 6/2002 | Liu et al. |
| 10,105,318 | B2 | 10/2018 | Psakhie et al. |
| 10,617,711 | B2 | 4/2020 | Smejkalova et al. |
| 2003/0102207 | A1 | 6/2003 | Wu et al. |

(Continued)

FOREIGN PATENT DOCUMENTS

| | | |
|---|---|---|
| EP | 3895831 A1 | 10/2021 |
| RU | 2048277 C1 | 11/1995 |
| RU | 2560432 C2 | 8/2015 |

(Continued)

OTHER PUBLICATIONS

Pustovalov, A.V.; Zhuravkov, S. P. Production of Iron Nanopowders by the Electric Explosion of Wire. Advanced Materials Research vol. 1097, p. 3-7. (Year: 2015).*
International Search Report for International Application No. PCT/RU2022/050004 mailed Jun. 3, 2022.
Written Opinion for International Application No. PCT/RU2022/050004 mailed Jun. 3, 2022.
International Search Report for International Application No. PCT/RU2022/050003 mailed May 20, 2022.
Written Opinion for International Application No. PCT/RU2022/050003 mailed May 20, 2022.

(Continued)

*Primary Examiner* — Jessica Worsham
(74) *Attorney, Agent, or Firm* — Perilla Knox & Hildebrandt LLP; Stephanie Davy-Jow; Kenneth A. Knox

(57) ABSTRACT

The given invention is related to the field of medicine, namely to experimental research in oncology, and can be used to obtain a pharmaceutical agent for inhibiting the proliferation of HeLa cervical cancer cells. It entails the use of a metal powder obtained in a gaseous medium by means of an electric explosion of a wire made of low-carbon steel carried out with a specific energy of 7-18 KJ/g and a pulse duration of 1.2-2 µs. The explosion is carried out inside a reactor that is pre-evacuated to a residual pressure of $10^{-2}$ Pa. and then filled with carbon monoxide to a pressure of $10^5$ Pa at a gas circulation rate flow of 10 m/s. The products of the explosion deposited in a hopper are passivated in air for at least 48 hours. The resulting powder is extracted and mixed with a solution of the RPMI-1640 nutrient medium with L-glutamine, a pH of 7.2, in the proportion of the mass of the powder to the volume of the specified solution from 1:10 to 2.7:10. The solution is then centrifuged until the phases are separated. The liquid phase is decanted and used as a pharmaceutical agent. The purpose of the given invention is to expand the arsenal of tools for inhibiting the proliferation of tumor cells.

1 Claim, 5 Drawing Sheets

(56)                   References Cited

U.S. PATENT DOCUMENTS

| | | |
|---|---|---|
| 2016/0074325 A1 | 3/2016 | Psakhie et al. |
| 2017/0143756 A1 | 5/2017 | Smejkalova et al. |

FOREIGN PATENT DOCUMENTS

| | | |
|---|---|---|
| RU | 2675188 C1 | 12/2018 |
| RU | 2686679 C2 | 4/2019 |
| RU | 2754617 C1 | 9/2021 |

OTHER PUBLICATIONS

Pustovalov Alexey V. et al: "Production of Iron Nanopowders by the Electric Explosion of Wire", Advanced Materials Research, vol. 1097, Jan. 1, 2015 (Jan. 1, 2015), pp. 3-7, XP055919013, DOI: https://www.scientific.net/AMR.1097.3.

Liu Lin et al: "Iron-Based Nanopowders Containing [alpha]-Fe, Fe 3 C, and [gamma]-Fe Particles Synthesised in Microwave Torch Plasma and Investigated with Mossbauer Spectroscop", Japanese Journal of Applied Physics Jpn. J. Appl. Phys, Jan. 1, 2011 (Jan. 1, 2011), XP055919381, Retrieved from the Internet: URL: https://iopscience.iop.org/article/10.1143/JJAP.50.08JF11/pdf.

Chen Zhang et al: "Synthesis of Iron Nanometallic Glasses and Their Application in Cancer Therapy by a Localized Fenton Reaction", Angewandte Chemie, Wiley-V CH Verlag GMBH & Co. KGAA, DE, vol. 128, No. 6, Jan. 6, 2016 (Jan. 6, 2016), pp. 2141-2146, XP071370226, ISSN: 0044-8249, DOI: 10.1002/ANGE. 201510031 the whole document & Zhang Chen et al: "Supporting Information Synthesis of Iron Nanometallic Glasses and Their Application in Cancer Therapy by a Localized Fenton Reaction", Angewandte Chemie, Jan. 1.

Kung Cheng et al: "Assessment of zero-valent iron-based nanotherapeutics for ferroptosis induction and resensitization strategy in cancer cells", Biomater. Sci. Biomaterials Science Paper Cite this: Biomater. Sci, Jan. 1, 2019 (Jan. 1, 2019), XP055919504, Retrieved from the Internet: URL:https://pubs.rsc.org/en/content/articlepdf/2019/bm/c8bm01525b.

Allwire. GOST 2246-70. https://all-wire.com/wire-gost-2246-70, Accessed Nov. 24, 2025.

Russian National Standard GOST 2246-70 "Steel welding wire", 2008.

* cited by examiner

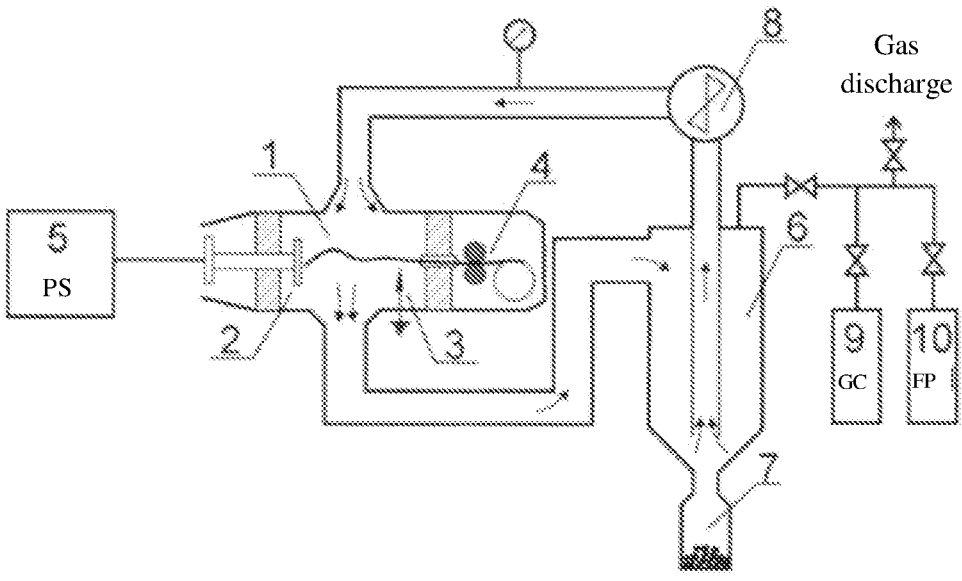
Fig. 1
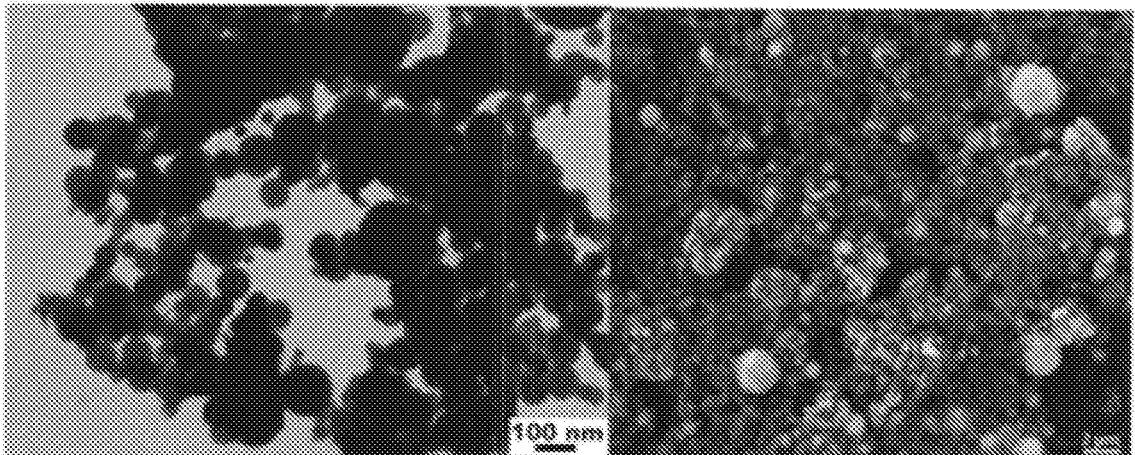
Fig. 2                                        Fig. 3

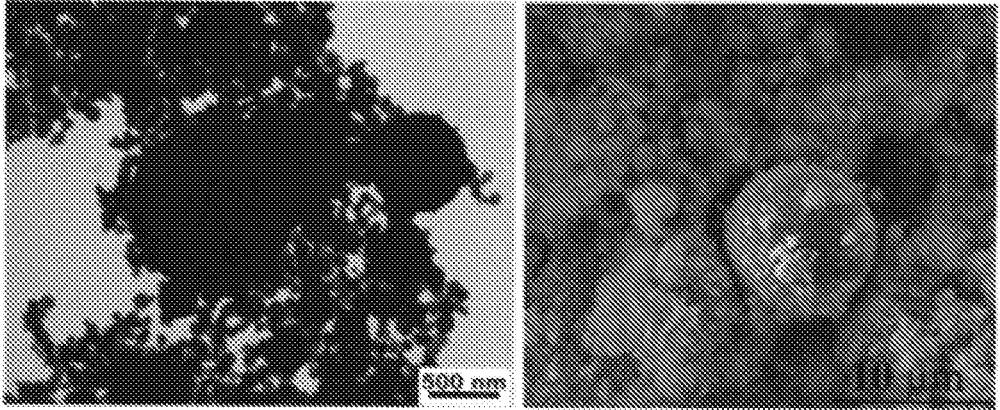
Fig. 7                                        Fig. 8
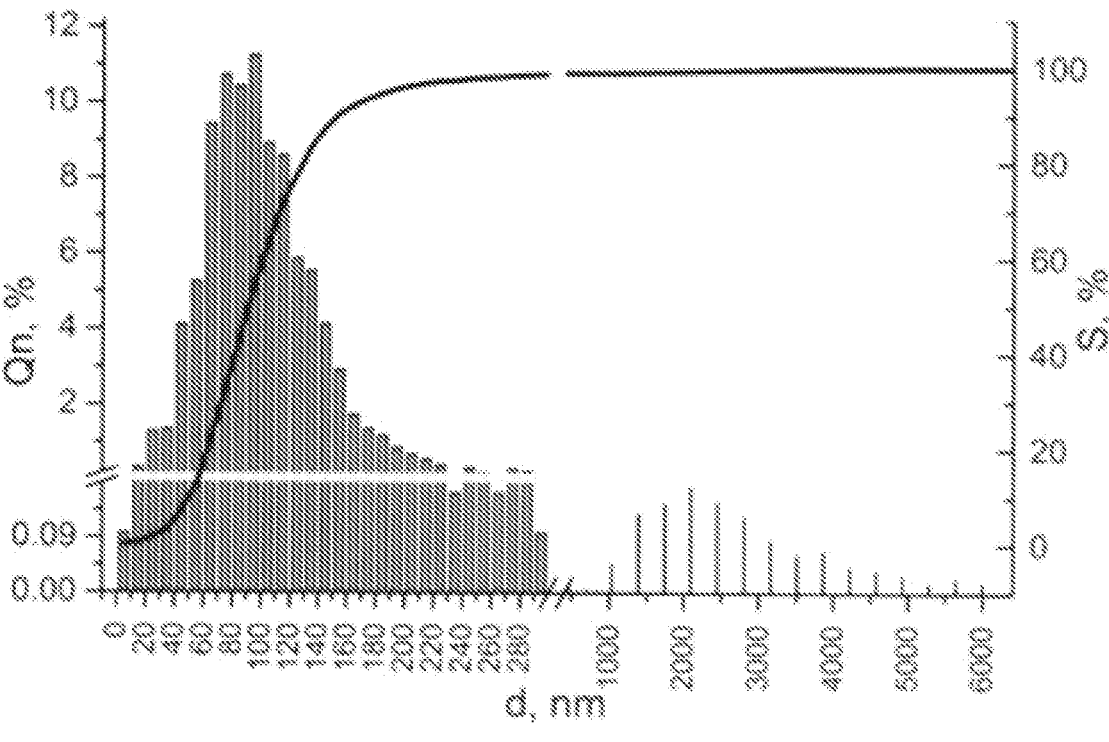
Fig. 9

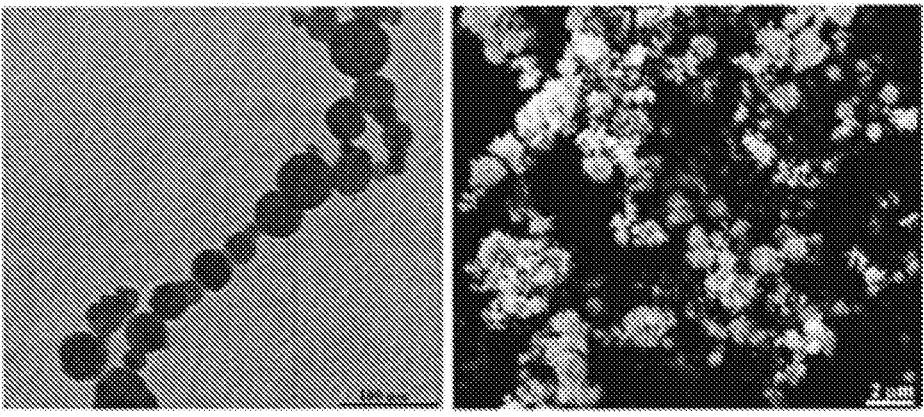
Fig. 10                          Fig. 11
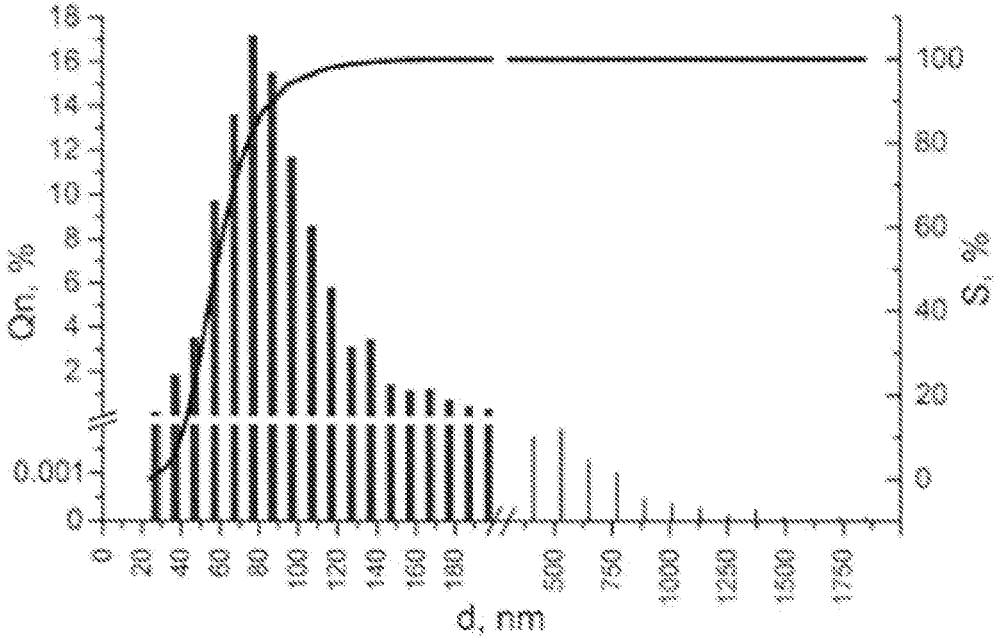
Fig. 12

METHOD OF OBTAINING A PHARMACEUTICAL AGENT USED FOR INHIBITING THE PROLIFERATION OF TUMOR CELLS

CROSS-REFERENCE TO RELATED APPLICATIONS

This application is a national phase application under 35 U.S.C. § 371 of International Application No. PCT/RU2022/050003 filed Jan. 10, 2022, entitled "METHOD OF OBTAINING A PHARMACEUTICAL AGENT USED FOR INHIBITING THE PROLIFERATION OF TUMOR CELLS," which claims the benefit of and priority to Russian Federation patent application No. 2021100394 filed Jan. 11, 2021, the contents of both of which being incorporated by reference in their entireties herein.

TECHNICAL FIELD

The present disclosure relates to medicine, namely to experimental research in oncology, and can be used to inhibit the proliferation of tumor cells.

BACKGROUND

A known method for producing an antitumor composition [RU 2686679 C2, MDK (2006.01) A61K 33/30, A61K 47/12, A61K 47/36, A61P 35/00, publ. Apr. 30, 2019] entails the preparation of an aqueous solution of an acylated derivative of hyaluronic acid with the subsequent addition of superparamagnetic nanoparticles dispersed in an organic halide solvent that is then stabilized with oleic acid. The resulting suspension is sonicated until a homogeneous mixture is formed. The free superparamagnetic nanoparticles are then separated from the superparamagnetic nanoparticles and loaded into nanomicelles by centrifugation and subsequent filtration. The filtrate is then lyophilized and sterilized by autoclaving in the final packaging. The lyophilisate can be dissolved in an aqueous solution and then autoclaved in the final packaging. Superparamagnetic nanoparticles ranging in size from 5 to 20 nm are nanoparticles based on iron oxides. The amount of iron in the composition ranges from 0.3 to 3 wt %.

The resulting composition may contain a medicinal drug and is selectively cytotoxic against both suspension and adhesive tumor cell lines, especially against the colorectal carcinoma and adenocarcinoma, lung carcinoma, hepatocellular carcinoma and breast adenocarcinoma tumor cell lines.

A known method of obtaining a pharmaceutical agent for inhibiting the proliferation of tumor cells [Example 2 from RU 2560432 C2, Mm {(2006.01) BOU 20/06, B82B 3/00, A61K 33/08246, publ. Aug. 20, 2015] was taken as a prototype. It entails the production of bimetallic Fe—Al nanoparticles with particle sizes of about 100 nm by means of a parallel electric explosion of an iron and aluminum wire in a nitrogen atmosphere at a Fe:Al ratio of 50:50 wt %. 20 g of the resulting powder is poured into 2,000 ml of distilled water and heated with constant stirring to 60° C., while the pH of the reaction mixture is controlled and maintained at 9.0 with an ammonia solution. The reaction was conducted for a period of 60 minutes. Then the suspension was filtered off, washed with distilled water until the wash water was neutral, and then dried at 90° C. for 4 hours.

The resulting pharmaceutical agent in the form of a powder is suspended in a growth agent and a mixture of trypsin:versene (at a ratio of 1:3) is added and used to suppress the proliferation of cancer cells, which is assessed by determining the proliferation index (the ratio of the number of grown cells to the number of seeded cells) after 48 and 72 hours.

BRIEF SUMMARY

The purpose of the disclosure is to expand the arsenal of tools for inhibiting the proliferation of tumor cells.

The method of obtaining a pharmaceutical agent for inhibiting the proliferation of cancer cells, as in the prototype, entails the use of a metal powder obtained by means of an electric explosion of a metal wire in a gaseous medium.

The present disclosure foresees an electric explosion of a wire made of low-carbon steel at a specific energy of 7-18 KJ/g and a pulse duration of 1.2-2 us inside a reactor that is pre-evacuated to a residual pressure of 10-2 Pa. The reactor is then filled with carbon monoxide to a pressure of 105 Pa at a speed of circulation of 10 m/s of the gas flow. The trapped products of the explosion are passivated in air for at least 48 hours. The resulting powder is extracted and mixed with a nutrient solution with a pH of 7.2, at a ratio of S:W from 1:10 to 2.7:10, then centrifuged until the phases are separated. The liquid phase is drained and used as a pharmaceutical agent.

RPMI-1640 medium with L-glutamine is used as a nutrient solution.

Under the proposed method, upon the creation of a metal powder, the metal iron nanoparticles interact with carbon monoxide as per the reaction:

$$Fe+5CO=Fe(CO)s$$

Since the products of the explosion are extracted into the hopper by gas flow, this reaction does not reach an end. The resulting product accumulates in the adsorption layer and remains on the surface of the solid nanoparticles.

To separate Fe (CO) s from unreacted metal particles, a nutrient solution was used as a solvent.

The use of the proposed pharmaceutical agent makes it possible to inhibit the proliferation of tumor cells with a proliferation index of less than 1.0 rel. units after 5-10 hours.

BRIEF DESCRIPTION OF THE DRAWINGS

Many aspects of the present disclosure can be better understood with reference to the following drawings. The components in the drawings are not necessarily to scale, with emphasis instead being placed upon clearly illustrating the principles of the disclosure. Moreover, in the drawings, like reference numerals designate corresponding parts throughout the several views.

FIG. 1 is a simplified circuit diagram of a Doherty power amplifier in the related art.

FIG. 1 shows a diagram of the rig for producing the metal powder.

FIG. 2 shows photographs of the particles of the powder obtained in Example 1.

FIGS. 3 and 4 show the particle size distribution of the powder obtained in Example 1.

FIGS. 7 and 8 show photographs of the particles of the powder obtained in Example 2.

FIG. 9 shows the particle size distribution of the powder obtained in Example 2.

FIGS. 10 and 11 show photographs of the particles of the powder obtained in Example 3.

FIG. 12 shows the particle size distribution of the powder obtained in Example 3.

DETAILED DESCRIPTION

Figure 4:
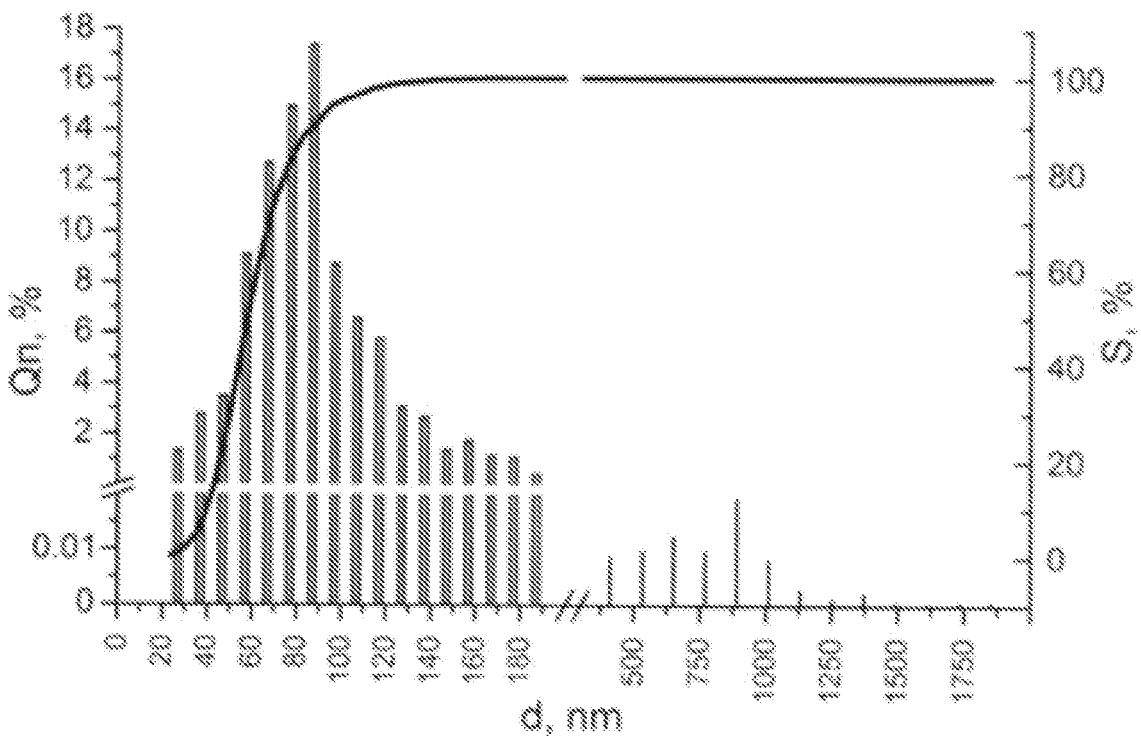

The rig for producing the metal powder consists of a horizontally installed reactor 1, which contains high-voltage 2 and grounded electrodes 3, as well as a feed mechanism 4 of the wire. The electrode 2 is connected to power supply 5 (PS). The bottom of the reactor 1 is connected by a pipeline to the inlet to the cyclone 6 of a cylindrical type, the lower part of which is equipped with a hopper 7 for collecting the powder. The outlet of the cyclone 6 is connected to the upper part of the reactor 1 by a pipeline, which contains the fan 8. The cyclone 6 is connected through pipelines equipped with valves to the gas cylinder 9 (GC) containing carbon monoxide, to the foreline pump 10 (FP) and to the valve 25 for discharging the gas.

Example 1

A coil of low-carbon steel wire of SV-08 grade alloy was placed in the wire feed mechanism 4 in the reactor 1. The diameter of the wire was 0.3 mm, and the length of the interelectrode gap was 80 mm.

Using a foreline pump 10 (FP), the internal volume of the rig was pre-evacuated to a residual pressure of 10-2. Then, from the gas cylinder 9 (GS), the internal volume of the rig was filled with carbon monoxide to a pressure of 105 Pa. By turning on the fan 8, carbon monoxide was continuously circulated through the pipeline connecting it to the reactor 1 at a speed of 10 m/s. Upon turning on of the feed mechanism 4, a continuous wire feed was injected in the direction from the grounded electrode 3 to the high-voltage electrode 2. The distance of the interelectrode gap was 80 mm. A high voltage with a duration of 1.5 us was applied to the high-voltage electrode 2 from the power source 5 (PS). When the wire injected into the reactor 1 came into contact with the high-voltage electrode 2, it exploded. The specific energy expended was 14 KJ/g. The products of the explosion of the wire were extracted by gas flow out of the reactor 1 into the cyclone 6, where they were separated from the carbon monoxide and deposited in the hopper 7. The purified gas from the cyclone 6 returned to the inlet of the fan 8 and entered the reactor 1 again. After the hopper 7 was filled with the accumulated products of the wire's explosion, the power source 5 (PS) was turned off, and the wire feeder 4, the fan 8 and the hopper 7 were disconnected from the cyclone 6. The hopper 7 was covered with a lid with an opening of a diameter of 1 mm and kept in this state for 48 hours to bring the resulting product into equilibrium. Afterwards, the resulting metal powder was removed from the hopper 7 and placed in a storage container.

The resulting metal powder is a mixture of nanoparticles ranging in size from 20 to 300 nm (FIG. 2, 3) with a maximum distribution of 80 nm and microparticles with a size of up to 2 μm and a maximum distribution of about 0.8 μm. In this case, the number of particles larger than 500 nm is no greater than 1% (FIG. 4).

Figure 5:
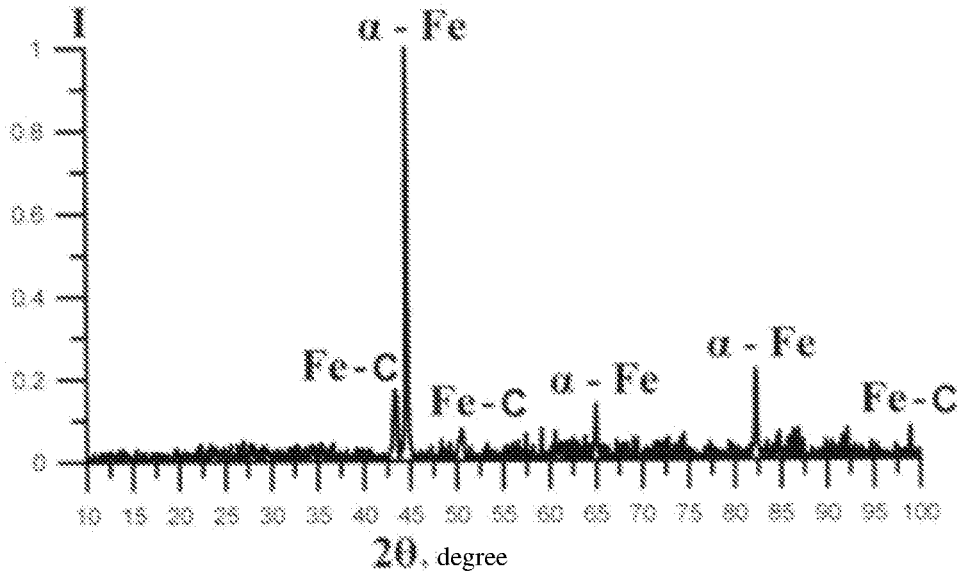
FIG. 5 shows an X-ray diffraction pattern obtained in Example 1 of the powder.

X-ray phase analysis showed that the obtained metal powder consists of pure iron particles in the form of a-Fe phase and austenite compound in the form of Fe—C (FIG. 5). Its specific surface area was 9.3 $m^2$/g.

Under sterile conditions, a 270 μg sample was taken from the obtained metal powder, and 1,000 μl of a nutrient solution RPMI-1640 with L-glutamine with a pH of 7.2 was added to it. The resulting mixture was stirred by ultrasound for 10 minutes in an ultrasonic bath—WiseClean—with an operating frequency of 300 kHz. Then the resulting suspension was centrifuged for 10 minutes in an Allegra 64R centrifuge (USA) at 3,000 rpm to separate the liquid and solid phases. The liquid phase, which is the end pharmaceutical agent, was poured into a container.

The resulting pharmaceutical agent was used for in vitro testing on Hela cells.

A HeLa cervical cancer cell line obtained from a Chinese hamster ovary CHO-KI was used for the experiment. The cells were kept in a wholesome nutrient medium-RPMI-1640-containing 10% inactivated fetal calf serum and antibiotics (50 U/ml penicillin and 50 μg/ml streptomycin), at 37° C., at 5% $CO_2$ content, in a humid environment (in a CO2 incubator).

The effect of the obtained pharmaceutical agent on epithelioid carcinoma of human cervical cancer HeLa cancer cells was carried out using a plate. The cells were seeded into the wells of an 8-well plate from the iCelligence system (ACEA Bioscience, USA) at the rate of 70 thousand cells per well.

4 hours after seeding of the cells, 200 μl of the obtained pharmaceutical agent was poured into some of the wells, and 200 μl of the RPMI-1640 nutrient solution were added to others.

The iCelligence real-time assessment system (ACEA Bioscience, USA) was used to determine the level of proliferation. The readings were taken in automated mode with an interval of 1 hour. The iCelligence system performed an automatic recalculation of the readings into the cell index, indicating the level of cell proliferation, as well as the calculation of the standard deviation. The data was statistically processed using the Statistica software.

Figure 6:
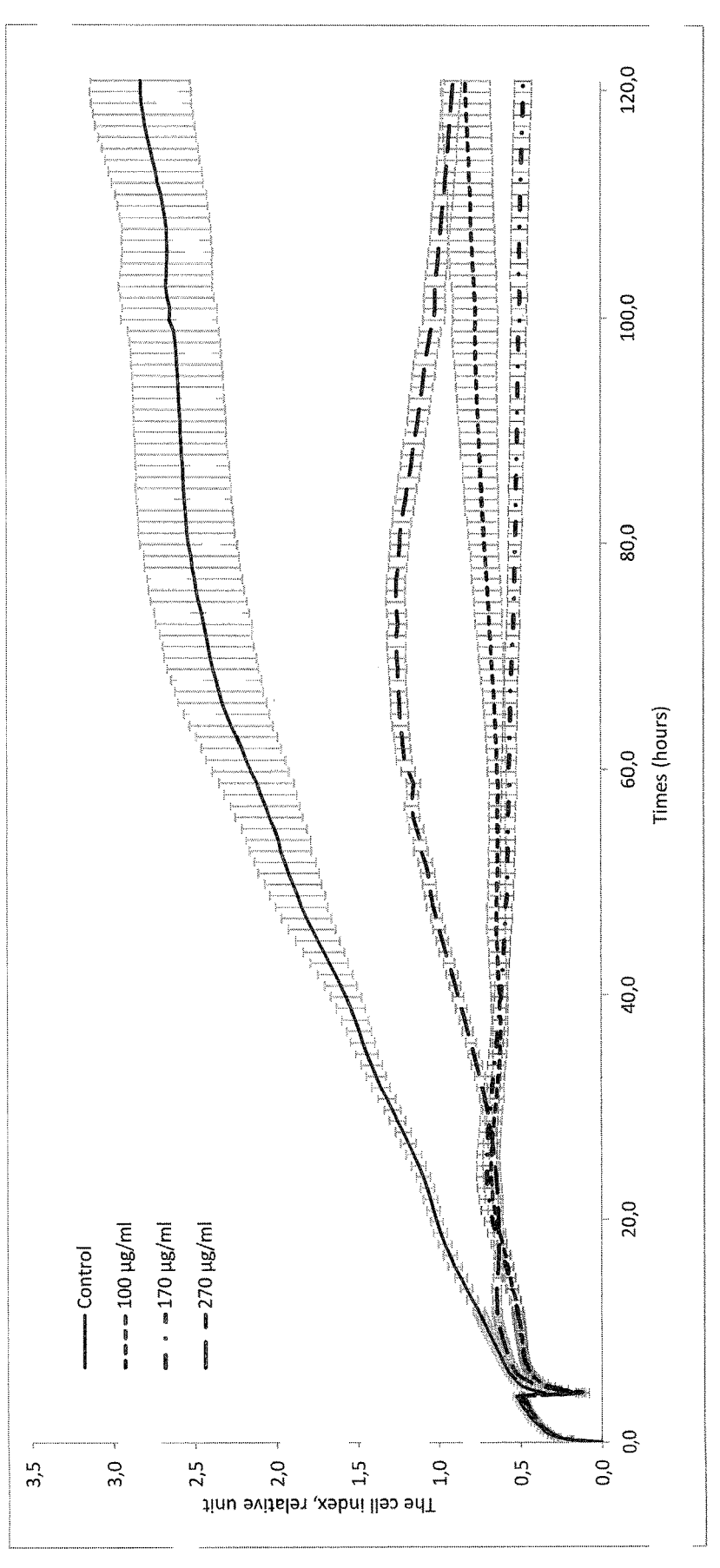
FIG. 6 illustrates the change in the cell index in Hela cells after the addition of a pharmaceutical agent.

The crimson curve (270 μg/ml) in FIG. 6 shows the inhibition of the proliferation of HeLa tumor cells relative to the control group (red curve). The inhibition of the proliferation of the tumor cells begins almost immediately after the addition of the pharmaceutical agent. The cell index was 0.5 rel. units, and 3.25 rel. units in the control group over 120 hours of observation.

Example 2

Under conditions similar to Example 1, an electric explosion of a workpiece with a diameter of 0.3 mm and a length of 80 mm was carried out on a low-carbon steel wire of SV08 grade alloy, at an energy supply of 7 KJ/g for 2 μs.

The corresponding images of the resulting powder particles are shown in FIG. 7 and FIG. 8.

The powder is a mixture of particles with a size of up to 6 microns and a maximum distribution of 2 microns and nanometer particles with a size of 20 to 300 nm with a maximum distribution of 80 nm.

The number of particles larger than 500 nm is more than 2% (FIG. 9). The phase composition of the resulting powder is the same as in Example 1 (FIG. 5). The specific surface area of this powder was 4 $m^2$/g.

Under sterile conditions, a sample weighing 100 μg was taken from the obtained metal powder, and 1,000 μl of a nutrient solution RPMI-1640 with L-glutamine with a pH of 7.2 was added to it. The pharmaceutical agent was prepared under the same conditions as in Example 1.

The resulting pharmaceutical agent was added to one of the wells at a rate of 100 μg/ml, and a nutrient solution was added to the control wells. The observation results are represented by the blue curve in FIG. 6 (100 µg/ml). The inhibition of the proliferation of the HeLa tumor cells relative to the red control curve begins almost immediately after the addition of the pharmaceutical agent. The cell index was 0.75 rel. units, and 3.25 rel. units in the control group over 120 hours of observation.

Example 3

Under conditions similar to Example 1, an electric explosion of a workpiece with a diameter of 0.3 mm and a length of 80 mm was carried out on a low-carbon steel wire of the SV08 grade alloy, at an energy supply of 18 KJ/g for 1.2 µs.

The corresponding images of the resulting powder particles are shown in FIG. 10, 11.

The resulting powder is a mixture of micron particles with a size of up to 2 µm and a maximum distribution of 500 nm and partially sintered nanoscale particles with a size of 20 to 300 nm with a maximum distribution of 80 nm. The number of particles larger than 500 nm is not more than 0.5% (FIG. 12). The phase composition of the powder is the same as in Example 1 (FIG. 5). The specific surface area of this powder was 11 $m^2/g$.

From the obtained powder, a weighed portion of 170 µg was taken and 1,000 µl of a nutrient solution RPMI-1640 with L-glutamine with a pH of 7.2 was added to it. Under the same conditions as in Example 1, a pharmaceutical agent was prepared. The resulting pharmaceutical agent was added to some of the wells at a rate of 170 µg/ml, and a nutrient solution was added to the control wells. The observation results are represented by a green curve in FIG. 6 (170 µg/ml). The inhibition of the proliferation of the HeLa tumor cells relative to the red control curve begins almost immediately after the addition of the pharmaceutical agent. The cell index is 0.75 rel. units, and 3.25 rel. units in the control group for 120 hours of observation.

The above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

The invention claimed is:

1. A method for obtaining a pharmaceutical agent for inhibiting proliferation of cervical cancer cells, comprising:

providing a metal wire made of a low-carbon steel;

providing a reactor that is pre-evacuated to a residual pressure of $10^{-2}$ Pa;

filling the reactor with carbon monoxide to a pressure of $10^5$ Pa at a circulation rate of a gas flow in the reactor of 10 m/s;

generating a metal powder obtained in a gaseous medium through an electric explosion of the metal wire, wherein the electric explosion is carried out at an energy of 7-18 KJ/g and a pulse duration of 1.2-2 us in the reactor;

depositing products of the electric explosion in a hopper and passivating the products in air for at least 48 hours, thereby creating a resulting powder;

extracting the resulting powder and mixing the resulting powder with a solution of a cell culture medium comprising nutrients sufficient to support mammalian cell growth with L-glutamine, the solution having pH of approximately 7.2, in a ratio of a mass of the resulting powder to a volume of the solution ranging from 1:10 to 2.7:10;

centrifuging the solution as mixed with the resulting powder until phases are separated; and decanting a liquid phase and obtaining the pharmaceutical agent therefrom.

\* \* \* \* \*